(12) United States Patent
Kuperus

(10) Patent No.: US 6,834,657 B1
(45) Date of Patent: Dec. 28, 2004

US006834657B1

(54) ABSORBANT PAD FOR APPLYING ANTI-COAGULANT

(76) Inventor: John Kuperus, 4209 Saltwater Blvd., Tampa, FL (US) 33615

( * ) Notice: Subject to any disclaimer, the term of this patent is extended or adjusted under 35 U.S.C. 154(b) by 98 days.

(21) Appl. No.: 10/364,639

(22) Filed: Feb. 12, 2003

(51) Int. Cl.[7] .................................................. B08B 1/00
(52) U.S. Cl. ............................... 134/6; 134/34; 134/42; 510/363; 510/438; 510/439
(58) Field of Search ................................ 134/6, 34, 42; 510/363, 438, 439

(56) References Cited

U.S. PATENT DOCUMENTS

| | | | | |
|---|---|---|---|---|
| 4,471,871 A | * | 9/1984 | Rockliffe et al. ........... | 206/205 |
| 5,762,948 A | * | 6/1998 | Blackburn et al. .......... | 424/404 |
| 5,871,692 A | * | 2/1999 | Haire et al. ................ | 422/28 |
| 6,429,183 B1 | * | 8/2002 | Leonard et al. ............. | 510/438 |
| 6,488,943 B1 | * | 12/2002 | Beerse et al. ............... | 424/401 |
| 6,489,284 B1 | * | 12/2002 | Suazon et al. .............. | 510/438 |
| 6,673,761 B2 | * | 1/2004 | Mitra et al. ................. | 510/384 |
| 6,764,988 B2 | * | 7/2004 | Koenig et al. .............. | 510/130 |

* cited by examiner

*Primary Examiner*—Sharidan Carrillo
(74) *Attorney, Agent, or Firm*—Stanley M. Miller

(57) ABSTRACT

A sterile, absorbent, lint-free, soft, and at least slightly abrasive pad is impregnated with an anti-coagulant. The pad is packaged in a sterile pouch and the pouch is opened to apply the anti-coagulant to an intravenous device such as a catheter or stent device, to clean blood from a used needle or to decontaminate an operating room surface. The anti-coagulant is preferably heparin-benzalkonium chloride formulated in a solution of 1.5% heparin-benzalkonium chloride by weight or volume, containing 850 USP heparin units per milliliter in a solvent such as isopropyl alcohol.

13 Claims, No Drawings

ABSORBANT PAD FOR APPLYING ANTI-COAGULANT

BACKGROUND OF THE INVENTION

1. Field of the Invention

This invention relates, generally, to means for applying an anti-coagulant to intravenous devices, needles, and operating room surfaces. More particularly, it relates to an anti-coagulant-containing pad and to methods for using the pad.

2. Description of the Prior Art

Heparin-quaternary ammonium compounds have been used for many years as non-thrombogenic coatings for catheters. The advent of nonionic intravenous contrast media has increased interest in the use of this material due to the lack of any of the antithrombogenic activity demonstrated by ionic contrast media. Heparin acts as an anti-coagulant, increasing the time a catheter or stent can remain inserted in the body without danger of a blood clot occluding or causing other problems with the procedure. Excessive amounts of heparin hemolyse (break apart) red blood vessels. Many catheters are now pre-coated by catheter manufacturers using the concentrations mentioned below.

Heparin coatings have been applied to catheters made with polyethylene, polyurethane, Teflon®, nylon, vinyl, and to stainless steel and Teflon-coated guidewires.

Additional uses for heparin coatings include vascular stents, tubing for heart-lung bypass machines, indwelling catheters and drains, renal dialysis tubing, and cell saver tubing.

Pre-coating of catheters is usually achieved by dipping the device into a coating solution, evaporating the solvent, which may be isopropyl alcohol, or other suitable solvent, and packaging the device.

Dipping catheters and other devices creates a thick coating. Some of these coatings can be thick enough to occlude small-bore catheters. The FDA has recalled some small bore catheters for this reason. Moreover, the coatings become brittle with age and may flake off, thereby reducing the shelf-life of such devices.

Thus a need exists for an improved method for coating catheters, stents, and other medical devices with an anti-coagulant in a way that does not occlude small bore catheters. The improved method should also extend the shelf-life of a coated device.

Nuclear pharmacies load brachytherapy needles with radioactive seeds and send such needles to hospitals for implantation of the seeds into the prostate glands of prostate cancer patients. From time to time, not all of the seeds are implanted and the hospital returns the bloodied needle containing unused seeds to the nuclear pharmacy that supplied the needle and seeds for proper radioactive material disposal. This is problematic because mixed waste (biohazardous and nuclear) is being sent through the mail. Moreover, the nuclear pharmacy may not be licensed to handle such mixed waste materials. Most nuclear pharmacies are not so licensed. An improved means is therefore needed for cleaning blood from needles.

Drapes and sheets are used to absorb blood from surgical procedures. Blood is the most common contaminate of stainless steel trays, surgical room floors, surgical table pedestals, etc. The cleanup process after an operation is extremely important. Current methods for cleaning and decontamination include the use of biocides and hand-scrubbing of surfaces to remove blood splatter or clotted pools of blood. The cleaning and disinfecting must be thorough and completed before the operating room is used again. Current methods of scrubbing down the operating room and removing blood residue therefrom are time-consuming, labor-intensive, and subject to failure if the workers are insufficiently fastidious in their approach to the job.

An improved method is therefore needed to remove blood and other contaminates from operating rooms, stainless steel trays, and other surfaces.

U.S. Pat. No. 6,488,943 to Beerse et al. discloses antimicrobial wipes that provide improved immediate germ reduction. The disclosure does not address the treating of medical devices with anti-coagulants or the removal of blood from needles or other surfaces. Similarly, U.S. Pat. No. 6,489,284 to Suazon et al. discloses a dishwashing cleaning wipe including a single layer needle punched fabric wherein the fabric is impregnated with a cleaning composition. U.S. Pat. No. 6,429,183 discloses a cleaning wipe that includes a nonwoven fabric that is impregnated with an antibacterial composition.

In view of the prior art considered as a whole at the time the present invention was made, it was not obvious to those of ordinary skill in the pertinent art how the identified needs could be met.

SUMMARY OF THE INVENTION

The long-standing but heretofore unfulfilled need for means for repairing the H-BAC coating on a catheter, stent, or other intravenous device, for cleaning needles, and for decontaminating surfaces is now met by a new, useful, and nonobvious invention.

The novel method for enhancing or repairing an anti-coagulant coating on a medical device such as a catheter or stent includes the steps of providing a sterile, absorbent, soft, lint-free and at least slightly abrasive pad. An anti-coagulant in a solvent is applied to the pad and the pad is packaged in a sterile pouch to prevent evaporation of the solvent or deterioration of the anti-coagulant. The pouch is opened when a medical device that may or may not have an H-BAC coating is to be inserted into a mammalian body. The device, which may be a catheter, a stent, or the like, is wiped with the pad to apply the anti-coagulant thereto. If the medical device was previously coated with an anti-coagulant, the wiping of said device with the at least slightly abrasive pad removes cracked or loose anti-coagulant coating from the device and deposits another coating of the anti-coagulant onto the device. This repairs and rejuvenates the device and facilitates subsequent coatings as well.

In a second novel method, a needle is decontaminated. A sterile, absorbent, soft, lint-free and at least slightly abrasive pad is provided and an anti-coagulant in a solvent is applied to the pad. The pad is packaged in a sterile pouch to prevent evaporation of the solvent or deterioration of the anti-coagulant. The pouch is opened when a needle is to be decontaminated after having been inserted into a mammalian body. The needle is wiped with the pad to apply the anti-coagulant to the needle. The wiping process removes blood from the needle.

In a third novel method, surfaces that may come into contact with blood are decontaminated by providing a sterile, absorbent, soft, lint-free, and at least slightly abrasive pad. An anti-coagulant in a solvent is applied to the pad and the pad is packaged in a sterile pouch to prevent evaporation of the solvent or deterioration of the anti-coagulant. The pouch is opened when blood is to be removed from a surface. The surface is wiped with the pad to apply the anti-coagulant to the surface. The at least slightly abrasive pad removes cracked or loose anti-coagulant coating that may have been on the surface and deposits another coating of the anti-coagulant to the surface to facilitate future cleaning of the surface.

In all three novel methods, the preferred anti-coagulant is heparin-benzalkonium chloride. In a preferred formulation, the heparin-benzalkoniun chloride is formulated in a solution of 1.5% heparin-benzalkonium chloride (wt/vol) in a preselected solvent and the solution contains 850 USP heparin units/ml. The solvent is preferably isopropyl alcohol.

An important object of this invention is to provide methods for repairing medical devices that are pre-coated with an anti-coagulant and for re-coating said devices with an anti-coagulant just prior to their use.

Another important object is to provide a method for cleaning a needle after use.

Another important object is to provide a method for decontaminating surfaces such as surgical room floors, trays, and other items in an operating room in a way that is faster and more effective than conventional decontamination methods.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

DETAILED DESCRIPTION OF THE PREFERRED EMBODIMENT

A measured quantity of an anti-coagulant such as heparin-benzalkonium chloride (H-BAC) is put onto a wipe with a suitable solvent such as isopropyl alcohol and is packaged in a pouch.

In all embodiments, the wipe preferably takes the form of an absorbent, soft, substantially lint-free, and at least slightly abrasive material, preferably in the form of a pad.

The pad is formed of a material selected from a group of materials consisting of continuous filament, knitted nylon, continuous woven polyester, nonwoven polyester, hydroentangled polyester, and nonwoven polyester/cellulose. The material should be non-shedding as well. The pad may also take the form of a nonwoven fabric, a single layer needle punched fabric, or the like, i.e., it may be of any suitable absorbent material that may be impregnated with a compound as long as the material exhibits the desired qualities of abrasiveness, softness, absence of lint, and the like. The pad need not be thick and may be as thin as a sheet of paper. In a preferred embodiment, the pad is gauze-like.

In a first embodiment, an anti-coagulant is applied to the pad and the pad is packaged in a sterile pouch to prevent evaporation of the solvent or deterioration of the anti-coagulant. The pouch is opened at a time prior to the moment when a medical device that may or may not have an H-BAC coating is to be inserted into a mammalian body. The exterior surface of the device, which may be a catheter, a stent, or any other intravenous device, is wiped with the pad to apply the anti-coagulant thereto.

If the medical device was previously coated with an anti-coagulant, the wiping of the device with the at least slightly abrasive pad removes cracked or loose anti-coagulant coating from the device and deposits a new, rejuvenating coating of the anti-coagulant to the device. This repairs and rejuvenates the device and facilitates its future coating as well.

If the device was not previously coated with an anti-coagulant, the wiping of the device with the novel anti-coagulant pad ensures that the device will have a suitable coating of anti-coagulant thereon prior to its insertion into the body. The introduction of a foreign device, such as a catheter, into the bloodstream can induce substantial clot formation on the device surface. With an untreated catheter, almost the entire surface may be covered with clots in the first twenty four (24) hours after catheter placement. This clotting tendency is greatly reduced, or completely eliminated, by coating the catheter with heparin. This greatly increases the patient's safety and thus reduces complaints against the physician and the hospital.

The preferred formulation of the H-BAC disclosed herein is substantially similar to the formulation of said anti-coagulant as used by catheter manufacturers. However, since the anti-coagulant is applied in the novel way disclosed herein, the dipping process of the prior art and the associated problem of occluding a catheter lumen is avoided. Also avoided are excessive heparin concentrations which may cause hemolysis of red cells which contact the thickly coated device.

In the second novel method, a needle is cleaned by wiping the needle with the novel anti-coagulant-treated pad. Although any needle requiring decontamination may be cleaned by this novel method, it has particular utility in cleaning needles that are covered with blood or other biohazardous bodily fluids and which need to be sent through the mail to a manufacturer. Prior to this disclosure, decontamination of such needles was problematic.

For example, brachytherapy needles are loaded with radioactive seeds and sent to hospitals for implantation of the seeds into the prostate glands of prostate cancer patients by nuclear pharmacies. From time to time, not all of the seeds are implanted and the hospital returns the bloodied needle containing the remaining seeds to the nuclear pharmacy that supplied the needle and the seeds for proper disposal of nuclear waste. Most nuclear pharmacies are not licensed to handle bio-hazardous mixed waste. This disclosure teaches that the novel pad having the heparin-benzalkonium chloride solution is advantageously used at the hospital to remove the blood or other fluids from the needle so that the hospital does not return biologically hazardous mixed waste to the nuclear pharmacy. The novel H-BAC abrasive wipe combination quickly and easily breaks down and removes any clotted blood residue on the needle, thereby solving a long-existing problem in the medical service and nuclear pharmacy industries.

Although the novel pad may be used as preferred by the user, the preferred method of use includes the steps of wiping the needle or catheter by placing the needle on the pad, folding the pad over the needle, and withdrawing the needle while the pad remains folded over the needle. This procedure efficiently applies the anti-coagulant to the needle and simultaneously scrubs the needle.

In the third novel method, surfaces that may come into contact with blood are decontaminated by wiping said surfaces with the novel anti-coagulant-containing pad before the surfaces become bloodied to preclude the blood from clotting on such surfaces. This facilitates post-operative clean-up and decontamination of all pre-treated, bloodied surfaces. Advantageously, continued, repeated use of the H-BAC wipe during clean-up puts another layer of heparin on the cleaned surface and thereby facilitates the next cleaning of the surface. The amount of anti-coagulant used in the wipes may be adjusted so that it is sufficient to hemolyse the red blood cells, thereby preventing their ability to dry, stain, and clot.

Significantly, since the anti-coagulant prevents blood from coagulating, drying, and staining a treated surface, the clean-up after an operation is not only much easier, it is also much faster. The time saved reduces the time between operations and thus increases the profitability of the operating room.

The three exemplary uses for the novel pad disclosed herein are not exhaustive and other uses for the novel pads are included within the scope of this invention. The concentration of H-BAC may be varied for specific purposes. For example, there may be a first concentration for wiping catheters, a second concentration for cleaning needles, a third concentration for wiping operation room floors, a fourth concentration for wiping trays and other surfaces, and so on. The abrasiveness of the pad may also be varied, depending upon the task. The pad may also be manufactured to vary in its absorbability, its softness, and other characteristics as well.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A method for decontaminating needles, comprising the steps of:

providing a sterile, absorbent abrasive pad;

applying an anti-coagulant to said pad;

packaging said pad in a sterile pouch to prevent deterioration of said anti-coagulant and to prevent evaporation of solvent;

opening said pouch when a needle is to be decontaminated after having been inserted into a mammalian body;

wiping said needle with said pad to apply said anti-coagulant to said needle;

and to remove blood and other body fluids from said needle.

2. The method of claim 1, wherein the step of wiping said needle includes the steps of placing said needle on said pad, folding the pad over the needle, and withdrawing the needle while said pad remains folded over said needle, thereby applying said anti-coagulant to said needle and simultaneously scrubbing said needle.

3. The method of claim 1, wherein the anti-coagulant is heparin-benzalkonium chloride.

4. The method of claim 1, wherein the pad is soft and substantially lint-free.

5. The method of claim 3, wherein the heparin-benzalkonium chloride is formulated in a solution of 1.5% heparin-benzalkonium chloride (wt/vol) and a preselected solvent.

6. The method of claim 3, wherein the preselected solvent is isopropyl alcohol.

7. The method of claim 3, wherein the heparin-benzalkonium chloride is formulated in a solution containing 850 USP heparin units/ml.

8. A method for decontaminating surfaces that may come into contact with blood, comprising the steps of:

providing a sterile, absorbent abrasive pad;

applying an anti-coagulant to said pad;

packaging said pad in a sterile pouch to prevent deterioration of said anti-coagulant and to prevent evaporation of solvent;

opening said pouch when blood is to be removed from a surface;

wiping said surface with said abrasive pad to remove a cracked or loose anti-coagulant coating previously present on said surface, wherein said wiping of said surface with said abrasive pad removes blood from said surface and deposits said anti-coagulant from said pad to said surface to form another coating of anti-coagulant onto said surface.

9. The method of claim 8, wherein the anti-coagulant is heparin-benzalkonium chloride.

10. The method of claim 8, wherein the pad is soft and substantially lint-free.

11. The method of claim 9, wherein the heparin-benzalkonium chloride is formulated in a solution of 1.5% heparin-benzalkonium chloride (wt/vol) and a preselected solvent.

12. The method of claim 9, wherein the heparin-benzalkonium chloride is formulated in a solution containing 850 USP heparin units/ml.

13. The method of claim 11, wherein the preselected solvent is isopropyl alcohol.

\* \* \* \* \*